United States Patent [19]

Pusineri

[11] 4,046,725
[45] Sept. 6, 1977

[54] POLYURETHANES FOR ARTICLES FOR MEDICAL USAGE

[75] Inventor: Christian Pusineri, Serezin du Rhone, France

[73] Assignee: Rhone-Poulenc Industries, Paris, France

[21] Appl. No.: 723,975

[22] Filed: Sept. 16, 1976

[30] Foreign Application Priority Data

Sept. 22, 1975 France .............................. 75.29467

[51] Int. Cl.$^2$ .............................................. C08L 5/10
[52] U.S. Cl. ........................................ 260/9; 424/183
[58] Field of Search ............................ 260/9; 424/183

[56] References Cited

U.S. PATENT DOCUMENTS

| | | | |
|---|---|---|---|
| 3,294,752 | 12/1966 | Wilkinson | 260/77.5 |
| 3,388,087 | 6/1968 | Dieterich et al. | 260/29.2 |
| 3,655,814 | 4/1972 | Rembaum | 260/77.5 |
| 3,755,218 | 8/1973 | Yen et al. | 260/9 |
| 3,766,104 | 10/1973 | Bonin et al. | 260/9 |
| 3,844,989 | 10/1974 | Harumiya et al. | 260/17.4 |
| 3,846,353 | 11/1974 | Grotta | 260/9 |
| 3,853,804 | 12/1974 | Yen et al. | 260/77.5 Q |

Primary Examiner—Edward M. Woodberry
Attorney, Agent, or Firm—Stevens, Davis, Miller & Mosher

[57] ABSTRACT

A polyurethane is disclosed which can be used in particular for the production of articles intended to be in contact with blood, characterized in containing a macromolecular chain comprising nitrogen atoms in the form of quaternary ammonium groups, to which molecules of heparin are bonded, these nitrogen atoms originating from polymers consisting of $q$ recurring units of the formula:

$$-A-NH-CO-O-B-O-CO-NH- \quad (I)$$

and $t$ recurring units of the formula:

$$-A-NH-CO-Z-NH- \quad (II),$$

these units of the formula (I) and (II) being bonded to one another, and the various symbols of these units having the following meanings:

A is a divalent organic radical consisting of a straight-chain or branched-chain alkylene radical containing from 3 to 10 carbon atoms, or a cycloalkylene radical having 5 or 6 carbon atoms in the ring or a phenylene radical which is optionally substituted by 1, 2 or 3 lower alkyl radicals (with at most 4 carbon atoms), or two alkylene or phenylene radicals linked to one another by a divalent hydrocarbon radical containing from 1 to 4 carbon atoms or by a hetero-atom chosen from amongst oxygen, sulphur and nitrogen, B represents a divalent organic radical obtained by removing the terminal hydroxyl groups from a macrodiol of the formula:

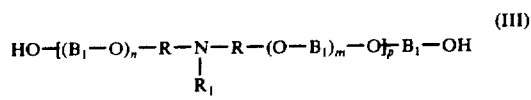

in which:

B$_1$ represents a linear or branched aliphatic radical having from 2 to 12 carbon atoms, R represents an alkylene radical of from 1 to 4 carbon atoms, R$_1$ represents an alkyl radical of from 1 to 20 carbon atoms which may contain functional groups, such as, for example, aldehyde, carboxylic acid or sulphonic acid groups, $n$, $m$ and $p$ are identical or different integers (or fractions in the case where (III) represents a mean formula) such that the molecular weight of B is between 300 and 10,000, and $q$ and $t$ are such that the polyurethane, before quaternization of the nitrogen atoms, has a specific viscosity, measured at 20° C on a solution of 2 g/l in dimethyl formamide, of greater than 0.05 and preferably between 0.1 and 0.9, the ratio $q/t$ being between 0.5 and 10, Z is a single bond or a divalent radical chosen from amongst the radicals of the formulae: —NH—NH—CO—, —NH—CH$_2$—CO—NH—NH—CO—, —NR$_2$—D—NR$_3$—CO—, and —O—M—O—CO—, in which R$_2$ and R$_3$, which may be identical or different, are hydrogen atoms or lower alkyl radicals, D is a hydrogen chain containing from 2 to 12 carbon atoms, or a hydrocarbon ring with 5 or 6 carbon atoms or a nitrogen-containing heterocyclic ring with 5 or 6 chain members, containing 1 or 2 nitrogen atoms, all the hydrocarbon chains and rings being saturated or unsaturated, unsubstituted or substituted by one or two lower alkyl radicals or by a nitrogen-containing heterocyclic ring with 5 or 6 chain members, which is attached by a nitrogen atom, it being possible for two of the chains or rings to be linked to one another by an alkylamino group, and M is an aliphatic hydrocarbon radical containing from 2 to 12 carbon atoms, which is linear or branched, saturated or ethylenically unsaturated, unsubstituted or substituted by one or two lower alkyl radicals or by a dialkylamino radical, which is uninterrupted or interrupted by an alkylamino radical. The polyurethane may comprise $t$ units of the formula (II) and $q$ units of the formula

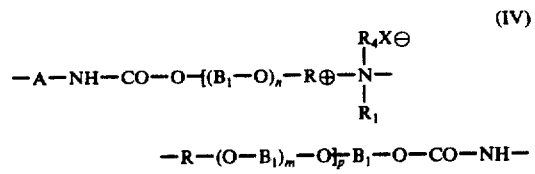

in which $R_4$ represents a monovalent or polyvalent organic radical and if R is monovalent, it may represent an alkyl, cycloalkyl or aralkyl radical which may possess functional groups and preferably containing fewer than 15 carbon atoms, these radicals being preferably the methyl, ethyl, propyl, cyclohexyl, benzyl and formylmethyl radicals, while if R is polyvalent it may represent an alkylene or alkenylene or cycloalkylene or aralkylene radical and then links different atoms or different macromolecular chains, and $X^{\ominus}$—is an anion, which anion may be replaced by another anion in accordance with the usual ion exchange techniques and is preferably an anion such as a halide (chloride, bromide or iodide), nitrate, sulphate, sulphite, phosphate, sulphonate and hydroxyl. The polymer may contain from 0.1 to 30 parts by weight of heparin per 100 parts of polymer. Processes for making the polymer; and shaped articles comprising the polymer are also included.

23 Claims, No Drawings

POLYURETHANES FOR ARTICLES FOR MEDICAL USAGE

The present invention relates to new non-thrombogenic polymers which have a retarding effect with regard to the coagulation of blood. These polymers furthermore possess valuable mechanical and elastic properties which permit their use in a variety of forms and in a variety of applications. They are used, in particular, for the manufacture of objects or articles which can be kept in contact with blood whilst substantially retarding coagulation of the latter; for example storage bottles, blood pouches, tubes, probes, cannulas, catheters and the like.

Non-thrombogenic polymers of the type of polyurethanes based on polyesters have already been proposed (U.S. Pat. No. 3,766,104).

One object of the present invention is to provide a non-thrombogenic polymers having improved stability and, in particular, improved resistance to hydrolysis.

Another object of the invention is to provide polymers having good non-thrombogenic properties.

It has now been found possible according to the present invention to achieve these and other objects with polymers which are polyurethanes, characterized in that they contain a macromolecular chain comprising nitrogen atoms in the form of quaternary ammonium groups, to which molecules of heparin are bonded, these nitrgen atoms originating from polymers consisting of $q$ recurring units of the formula:

$$-A-NH-CO-O-B-O-CO-NH- \qquad (I)$$

and $t$ recurring units of the formula:

$$-A-NH-CO-Z-NH- \qquad (II),$$

these units of the formula (I) and (II) being bonded to one another, and the various symbols of these units having the following meanings:

A is a divalent organic radical consisting of a straight-chain or branched-chain alkylene radical containing from 3 to 10 carbon atoms, or a cycloalkylene radical having 5 or 6 carbon atoms in the ring, or a phenylene radical which is optionally substituted by 1, 2 or 3 lower alkyl radicals (i.e., having at most 4 carbon atoms), or two alkylene or phenylene radicals linked to one another by a divalent hydrocarbon radical containing from 1 to 4 carbon atoms or by a hetero-atom chosen from amongst oxygen, sulphur and nitrogen;

B represents a divalent organic radical obtained by removing the terminal hydroxyl groups from a macrodiol of the formula:

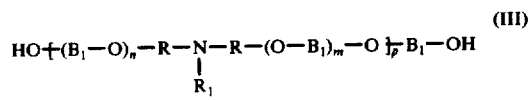

$$HO \!+\! (B_1-O)_n-R-N-R-(O-B_1)_m-O \!+\! _p B_1-OH \qquad (III)$$
$$\qquad\qquad\qquad\qquad | \\ \qquad\qquad\qquad\qquad R_1$$

in which:

$B_1$ represents a linear or branched aliphatic radical having from 2 to 12 carbon atoms, R represents an alkylene radical of from 1 to 4 carbon atoms, $R_1$ represents an alkyl radical of from 1 to 20 carbon atoms which may contain functional groups, such as, for example, aldehyde, carboxylic acid or sulphonic acid groups, $n$, $m$ and $p$ are identical or different integers (or fractions in the case where (III) represents a mean formula) such that the molecular weight of B is between 300 and 10,000, and $q$ and $t$ are such that the polyurethane, before quaternization of the nitrogen atoms, has a specific viscosity, measured at 20° C on a solution of 2 g/l in dimethylformamide, of greater than 0.05 and preferably between 0.1 and 0.9, the ratio $q/t$ being between 0.5 and 10, Z is a single bond or a divalent radical chosen from amongst the radicals for the formulae: $-NH-NH-CO-$, $-NH-CH_2-CO-NH-NH-CO-$, $-NR_2-D-NR_3-CO-$ and $-O-M-O-CO-$, in which $R_2$ and $R_3$, which may be identical or different, are hydrogen atoms or lower alkyl radicals, D is a hydrocarbon chain containing from 2 to 12 carbon atoms, or a hydrocarbon ring with 5 or 6 carbon atoms or a nitrogen-containing heterocyclic ring with 5 or 6 chain members, containing 1 or 2 nitrogen atoms, all the hydrocarbon chains and rings being saturated or unsaturated, unsubstituted or substituted by one or two lower alkyl radicals or by a nitrogen-containing heterocyclic ring with 5 or 6 chain members, which is attached by a nitrogen atom, it being possible for two of the chains or rings to be linked to one another by an alkylimino group, and M is an aliphatic hydrocarbon radical containing from 2 to 12 carbon atoms, which is linear or branched, saturated or ethylenically unsaturated, unsubstituted or substituted by one or two lower alkyl radicals, which is uninterrupted or interrupted by an alkylimino radical.

The polymers according to the invention are obtained from a polyurethane containing tertiary nitrogen atoms in units of the formula (I), this polyurethane with tertiary nitrogen atoms being subjected to a quaternization treatment followed by a heparination treatment.

The base polyurethane is prepared from a macrodiol of the formula HO—B—OH, in which B corresponds to the formula (III); in accordance with the usual process, this macrodiol is reacted with a diisocyanate to give a macrodiisocyanate, which is then subjected to the action of a coupling agent, to form the polyurethane.

The macrodiols HO—B—OH are preferably prepared from an aminodiol of the general formula HO—R—N(R$_1$)—R—OH in which the radicals R and R$_1$ correspond to the above-mentioned definitions. For this purpose, this aminodiol is reacted either with an epoxide such as ethylene oxide or propylene oxide, or with a cyclic ether of a diol, such as tetrahydrofurane, or with a glycol such as ethylene glycol, diethylene glycol, triethylene gylcol, the propanediols, butanediol, hexanediol and the like. This preparation of the polyethers is carried out under the conditions usually employed in the art. The amounts of aminodiol and of epoxide or of glycol employed are chosen in accordance with the content of tertiary nitrogen which the desired polymer must have. By using several epoxides and/or diols, copolyethers are obtained which can also be used in the invention.

The macrodiisocyanate is prepared by reacting a polyether with a diisocyanate of the formula O=C=N—A—N=C=O, wherein A corresponds to the definition given above, the amounts of macrodiol and of diisocyanate being so chosen that the ratio of the isocyanate groups to hydroxyl groups is greater than 1 and preferably between 1.5 and 3. Amongst the diisocyanates which can be used there may be mentioned: 1,6-diisocyanatohexane, 2,4-diisocyanatotoluene, 2,6-diisocyanatotoluene, meta-diisocyanatobenzene, 2,2-bis-(4-isocyanato-cyclohexyl)-propane, bis-(4-isocyanato-cyclohexyl)-methane, 1,5-diisocyanatopentane, 1,4-diisocyanatocyclohexane and, advantageously, bis-(4-isocyanatophenyl)-methane. It does not go outside the scope of the invention to use a mixture which contains one or more diisocyanates, and to introduce up to 10% of the isocyanate groups by means of one or more compounds which contain from 3 to 8 isocyanate groups per molecule.

The reaction for the preparation of a macrodiisocyanate, of a polyether with a di(or poly)isocyanate, is in general carried out at a temperature between 20° and 150° C; it can be carried out in bulk or in the presence of an inert and anhydrous solvent such as anhydrous toluene or dimethylformamide; it is possible to add a catalyst such as those mentioned by J.H. Saunders and K. C. Frisch in *Polyurethane Chemistry and Technology*, Part 1, pages 165-170 (1962).

The coupling agent is a compound with active hydrogen atoms known for the purpose of lengthening polyurethane chains by reactions with the isocyanate groups of these polymers. This agent can be chosen from a great variety of categories of chemical compounds. According to the invention, it is preferred to use water, hydrazine, amino-acetic acid hydrazide, a diamine or a diol. The diol used can be a diol of the formula HO—M—OH, where M has the meaning given above.

As example of the diols there may be mentioned 1,2-ethanediol; 1,2- and 1,3-propanediol; 1,2-, 1,3- and 1,4-butanediol; 1,5-pentanediol; 1,6-hexanediol; 1,10-decanediol; 2,2-dimethyl-1,3-propanediol; 2,2diethyl-1,3-propanediol; and butenediol.

It is also possible to choose a diamine as the coupling agent. The latter has the general formula $HR_3N—D—NR_2H$, wherein $R_3$, $R_2$ and D correspond to the above-mentioned definitions; it can be a primary or secondary diamine. Amongst numerous suitable amines there may be mentioned ethylenediamine; 1,2-diaminopropane; 1,6-diaminohexane; the phenylenediamines; the diaminocyclohexylmethanes; and the diaminocyclohexylpropanes.

The coupling reaction is preferably carried out in a solvent consisting wholly or partly of a polar aprotic solvent such as dimethylformamide; dimethylacetamide; dimethylsulphoxide; or tris-(dimethylamino)-phosphine oxide. It is carried out at temperatures which can vary from −20° to 100° C, depending on the reactants employed.

Polymers are thus obtained whereof the specific viscosity, measured at 20° C on a solution containing 2 g/liter in dimethylformamide, is greater than 0.05 and preferably between 0.1 and 0.9.

As has been stated, the tertiary nitrogen atoms of the polymer obtained are then subjected to a quaternization.

The quaternizing agents used are generally monoquaternizing agents, such as the esters of inorganic acids, preferably alkyl, cycloalkyl or aralkyl halides and sulphates. The compounds in which the alkyl, cycloalkyl or aralkyl radical contains at most 14 carbon atoms are particularly suitable. In particular, methyl, ethyl, propyl, cyclohexyl and benzyl chloride, bromide and iodide, dimethyl sulphate or diethyl sulphate may be mentioned. Halogen derivatives containing other chemical functional groups, such as chloroacetaldehyde or bromoacetaldehyde and esters and salts of halogen-containing acids, are also suitable.

It is also possible to use polyquaternizing agents such as the polyhalogenated derivatives of alkanes, alkenes, cycloalkanes or arylalkanes, especially alkylene, alkenylene, cycloalkylene or arylalkylene dichlorides, polyhalogenated organic polymers or polyhalogenated organosilicon compounds. As examples of such agents there may be mentioned, 1,3-dichloropropane; 1,3-dibromopropane; 1,4-dichlorobutane; 1,4-dibromobutane; 1,4-diiodobutane; 1,4-dichlorobut-2-ene; bis-(chloromethyl)- xylene; 1,3-bis-(chloromethyl)-1,1,3,3-tetramethyl-disiloxane; and the polyepichlorohydrins.

It is possible to start the quaternization with a monoquaternizing agent and thereafter to use a polyquaternizing agent, or vice versa.

It is also possible to carry out a partial quaternization of the polymer with the above-mentioned agents and then to treat the polymer with a quaternizing agent with functional groups so as to modify its properties. For this purpose it is possible to use a lactone such as butyrolactone or a sultone, for example propanesultone. By means of these compounds, carboxylic acid groups or sulphonic acid groups are introduced into the polymer, and these groups are capable of modifying the structure of the polymer by ionic crosslinking, which has the effect of modifying the elastic and mechanical properties of the treated product. This crosslinking in particular brings about a change in the swelling capacity of the polymer in water and in various solutions or solvents. It is thus possible to obtain, by means of these agents, a polymer having a defined swelling capacity, by experimentally establishing the ratio of the various reactants. The content of quaternary ammonium groups in the polymer can vary within wide limits and can range from 0.01 to 0.8 group per 100 g of polymer.

The quaternization is generally carried out by bringing the quaternizing agent into contact with the polymer containing tertiary nitrogen atoms, the polymer usually being in solution, at a temperature between 0° and 150° C and preferably between 20° and 110° ; C.

It is also possible to quaternize before polycondensing; that is to say, it is possible to quaternize the macrodiol of formula (II) so as to attach an $R_4$ monovalent radical to the nitrogen atom (the meaning of $R_4$ is given below but here, preferably, $R_4$ is an alkyl radical); then the quaternized macrodiol is caused to react with the diisocyanate so as to produce a quaternized macrodiisocyanate; this macrodiisocyanate is then caused to react with the coupling agent so as to produce directly the quaternized but non-heparinated polyurethane.

The quaternized but non-heparinated polyurethane which is involved in the structure of the polymers according to the invention thus comprises $t$ units of formula (II) and $q$ units of the formula:

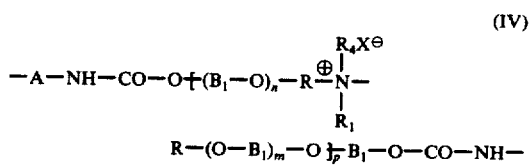

in which the various symbols have the meanings already given, and $R_4$ represents a monovalent of polyvalent organic radical; if $R_4$ is monovalent, it may represent an alkyl, cycloalkyl or aralkyl radical preferably containing fewer than 15 carbon atoms; as radicals of this type there may be mentioned the methyl, ethyl, propyl, cyclohexyl and benzyl radicals; these monovalent radicals may optionally contain functional groups, for example formyl groups; formylmethyl may be mentioned as a radical of this latter type. If $R_4$ is polyvalent, it may for example represent an alkylene or alkenylene, or cycloalkylene or aralkylene radical. When the radical $R_4$ is polyvalent, it joins different nitrogen atoms of different marcromolecular chains; if $R_4$ is monovalent and carries functional groups, these groups can optionally react and themselves give rise to additional crosslinks.

$X^-$ is an anion; this anion may be replaced by another anion in accordance with the usual ion exchange techniques; amongst the most common anions there may be mentioned the halides (chloride, bromide and iodide), nitrate, sulphate, sulphite, phosphate, sulphonate and hydroxyl.

It should be inidicated that the units of the formula (II) and (IV) are bonded to one another in such a way that the end group A of one is linked to the end group NH of the other and vice versa. This is furthermore also the case for the units of the formula (I) and (II) which are linked to one another in accordance with the same rule.

The fixing of heparin (heparination) to the polymers having quaternary ammonium groups is carried out by bringing the polymer (in the solid state or in solution) into contact with a solution containing heparin. This heparination may take place before, during, or after the shaping of the polymer. The heparin may be used in the acid form or in the form of a salt of an alkali metal or alkaline earth metal. However, the heparin is most commonly used in the form of a sodium salt, which is both more stable and more readily available commercially. The heparin solution can be an aqueous or an aqueous-organic solution.

When the heparination is carried out before shaping the polymer, the latter is generally in the form of a solution, to which a solution of heparin is added, the solvents of the heparin solution and of the polymer solution being miscible with one another. Depending on the concentrations of the solutions and on the amounts employed relative to the polymer, it is possible to fix amounts of heparin ranging, for example, from 0.1 to 30 parts by weight, or even more, per 100 parts of polymer. If the polymer according to this invention is intended to be maintained in contact with blood for long periods, it is preferred to fix from 16 to 30 parts by weight of heparin relative to 100 parts of the polymer; if the polymer is intended to be maintained in contact with the blood for only relatively short periods, it is preferred to fix 0.5 to 20 parts by weight of heparin relative to 100 parts of the polymer.

It is also possible to carry out the treatment with heparin after the shaping of the polymer. This after-treatment may be carried out by immersing the article in a heparin solution, or by coating its surface with the heparin solution (for example by spraying or painting). In this case, the concentration of the heparin solution as well as the duration and temperature of the treatment may vary over wide limits; in general, it is preferred to work at a temperature of between 20° and 40° C, with a heparin solution of which the concentration is from 0.2 to 500 g/liter. The duration of the treatment is in general between 1 minute and 4 hours depending on the temperature and on the concentration of the heparin solution. It is possible to carry out several successive coatings with the heparin solution.

The polymers of the present invention may be associated with other polyfunctional polymers; more precisely, with anionic polyelectrolytes capable of bonding ionically to the free quaternary ammonium sites. This association has the object of modifying certain properties of the polyurethanes and in particular makes it possible to modify their swelling capacity and thus to vary the rate of diffusion of the heparin. This association of anionic and cationic polymers in order to form complex polyelectrolytes has been described in Belgian Pat. No. 785,741; the anionic polyelectrolytes may be chosen from amongst those mentioned in that patent and the conditions for their preparation may be those described in this patent. The vinyl polymers having a plurality of sulphonic acid groups, and the sulphonated polymers, especially the sulphonated polysulphones, mentioned in the Belgian patent, are particularly suitable.

The polymers of this invention have good mechanical and elastic properties; their resistance to hydrolysis and to certain chemical reagents and solvents makes them of value for the manufacture of surgical articles which mast be sterilized by the usual processes, in particular by means of gamma-rays or ethyl alcohol. Because of their anticoagulant activity of blood, the polymers can be used for the manufacture of articles which must be kept in more or less prolonged contact with blood, in particular materials for transfer or storage. These shaped objects or articles may consists throughout of polymers according to this invention, or the polymers according to the present invention may merely constitute a surface coating, which coating can itself be of greater or lesser thickness. When such shaped objects or articles are produced, the polymers according to the invention may be coated or molded, this coating or molding employing solutions or, where appropriate, polymers in a semi-molten state.

A particular object of this invention further resides in a process of heparination of polymer which in particular makes is possible to arrive at polymers having a high heparin content, especially within the mass of the polymer.

The heparination, in the mass, of polymers carrying quaternary ammonium groups and especially of hydrophilic polymers, for example polyurethanes carrying quaternary ammonium groups, is advantageously carried out in an organic solvent. For these polyurethanes carrying quaternary ammonium groups and also for other polymers it is advantageous (especaill because of solubilities) to use solutions thereof in polar aprotic solvents, especially dimethylformamide (DMF) or dimethylacetamide (DMAc) or the like.

However, heparin in the form of its sodium salt is not soluble in such solvents. A process has now been found which makes it possible to heparinate the polymers in solution in polar aprotic solvents. This process is characterized in that the heparination, that is to say the bringing into contact of the heparin (in the sodium salt form) with the polymer to be treated, is carried out in the presence of water and of a solvent chosen from the group consisting of dimethylsulphoxide (DMSO) and diethylene glycol (DEG). In the text which follows, the parts mentioned are parts by weight. Preferably, 50 to 1,000 parts of water and 50 to 1,000 parts of DMSO or DEG are used per 100 parts of heparin, and the heparination may be carried out in the presence of a third solvent (especially an aprotic polar solvent) for the polymer to be treated, for example DMF or DMAc or mixtures containing a substantial proportion of these solvents. Preferably, between 100 and 200 parts of water and between 300 and 1,000 parts of DMSO or DEG are used per 100 parts of heparin. The various proportions of solvents are also chosen such as to give a homogeneous mixture during heparination. Thus it is preferred that the ratio of parts of water/parts of DMSO or DEG should be less than 1.

After bringing the heparin into contact with the polymer to be treated, in the solvents and under the conditions defined above, a heparinated collodion, that is to say a homogeneous solution containing the heparinated polymer, solvents and possibly heparin is obtained. The heparinated collodion is advantageously used directly for coatings or for the production of shaped articles based on heparinated polymer. After casting or coating, evaporation or coagulation is carried out so as to convert the heparinated polymer to the solid state.

The examples which follow illustrate still further the preparation of the polymers according to the present invention.

EXAMPLE 1

(Preparation of a Polyurethane)

333 g (2.5 mols) of N-ethyl-diethanolamine and 8.32 g of potassium hydroxide are introduced, under a nitrogen atmosphere, into a 7,500 cm³ autoclave equipped with a nitrogen inlet and a stirrer system, and are heated to 95° C until solution is complete. After cooling, the reaction mixture is dehydrated by heating at 80°-82° C under a vacuum of 13 mm, and the temperature is then raised to 110°-112° C and propylene oxide is injected, the pressure being maintained at between 4 and 5 bars. The amount of propylene oxide introduced after 8 hours is 2,480 g (42.75 mols). The reaction mixture is kept at this temperature for a further 2 hours and the propylene oxide which has not reacted (120 g) is then removed by distillation in vacuo.

The polyether thus obtained contains 0.936 milliequivalent/gram of tertiary nitrogen. This polyether is neutralized by the slow addition of concentrated hydrochloric acid until the pH is 6-7, the reaction mixture is then dehydrated by heating at 80° C under a vacuum of 13 mm Hg (absolute pressure) and the potassium chloride formed is filtered off. The polyether thus obtained has a molecular weight of 1,065.

422.5 g (1.69 mols) of di-(4-isocyanatophenyl)-methane are added slowly, under an atmosphere of an inert gas, to 900 g of the above polyether, which has been heated to 80° C, and the mixture kept at this temperature, whilst stirring, for 45 minutes. The macrodiisocyanate thus obtained is cooled and then dissolved in 750 cm³ of dimethylformamide (in the case of all the operations in the examples, the solvent has beforehand been distilled over molecular sieves).

Thereafter, a solution of 37.6 g (0.422 mol) of aminoacetic acid hydrazide in 1,740 g of dimethylformamide is prepared by heating at 60° C. 1,015 g of the macrodiisocyanate solution prepared as described above are slowly run into the cooled hydrazide solution, whilst stirring (duration of addition 1 hour 45 minutes) and the mixture is diluted by adding 1,890 g of dimethylformamide. The solution of polyurethane thus obtained is poured slowly, with vigorous stirring, into a mixture of 8 kg of ice and 24 kg of water containing 128 g of sodium hydroxide, in order to precipitate the polymer. The latter is filtered off, washed with water until neutral, and dried in vacuo at 40° C and then over phosphorus pentoxide, at ambient temperature, to constant weight. 682 g of a polyurethane containing 0.583 milliequivalent/g of tertiary nitrogen (acidimetric determination) are thus obtained.

(Preparation of the Heparin-Treated Product)

256 g of the polyurethane just described are dissolved in 1,344 g of dimethylformamide and 85 g of methyl iodide are added to this solution. The mixture is stirred for 15 minutes at ambient temperature and then for 9 hours 30 minutes at 45°-47° C. After cooling, it is run into a mixture of 7.5 kg of ice and 25 kg of water. The polymer which precipitates is filtered off, washed with water and then with methanol, and dried, as above, to constant weight. The degree of quaternization, determined by acidimetric determination, is 100%. The polymer contains 0.583 milliequivalent of quaternary nitrogen per gram.

A solution of 3.6 g of heparin, in the form of its sodium salt, in 6.3 cm³ of water is prepared and 31.5 cm³ of dimethylsulphoxide are added. This mixture is run slowly into a solution of 18 g of the quaternized polyurethane just described in 82 g of dimethylformamide, and the mixture is stirred for 2 hours. A homogeneous solution of a polyurethane containing 16.6% by weight of heparin is thus obtained.

A film of this polymer (35 × 25 cm) is prepared by casting the solution onto a glass plate (thickness of the liquid film: 1 mm). After drying at 50° C under a pressure which has been reduced to 200 mm Hg, for 2 hours, 60% of the solvents have been removed. This film is immersed in absolute alcohol in order to remove the residual solvents and is then treated for 1 hour at 40° C under a pressure reduced to 100 mm Hg in a water-saturated atmosphere and then rinsed with 3 liters of water to remove the alcohol.

The film thus obtained exhibits 40% swelling in water. 20 cm² of this film are rinsed with 1 liter of physiological liquid (water containing 9 g/l of NaCl) and then immersed in 20 cm³ of dog's blood plasma containing citrate. The heparin is gradually liberated into the plasma. The following contents of heparin liberated into the plasma are observed as a function of time.

| Time | Heparin Liberated in mg/l |
| --- | --- |
| 0 | 0 |
| 30 mins. | 0.96 |
| 1 hour | 1.15 |
| 2 hours | 1.25 |
| 4 hours | 1.4 |

EXAMPLE 2

34 g of the polyurethane quaternized with methyl iodide, prepared according to the preceding example, the quaternary nitrogen content being 0.583 milliequivalent/g, are taken. This polymer is mixed with 1.78 g of a sulphonated polysulphone having an ionic capacity of 1,110 milliequivalents of sulphonic acid sites/g, which amount makes it possible to neutralize 10% of the quaternary ammonium sites. Thereafter 107 g of dimethylformamide are added and the mixture is stirred at ambient temperature until dissolved.

Separately, 3.58 g of heparin (in the form of its sodium salt) are dissolved in 6.3 cm³ of water and this solution is diluted with 31.5 cm³ of dimethylsulphoxide. This solution is poured dropwise into the preceding solution and the mixture is left to stand.

A film of size 35 × 25 cm is prepared from this solution under the conditions described in the above Example 1.

The anticoagulant activity of the polymer thus obtained is measured in accordance with the FOURT method. For this purpose, a 20 × 20 cm film is folded in the shape of a cone or cornet. This cone is then itself placed in a glass cone immersed to the extend of 2/3 in a bath thermostatically controlled to 37° C. 25 cm³ of an aqueous solution containing 9 g/l of NaCl are poured into the heparinated polyurethane cone and are replaced, after 30 minutes, by 2 cm³ of venous blood coming from a fresh puncture carried out on a rabbit. The time required for complete coagulation is measured. After 1 hour's contact with the heparinated film, the blood has not coagulated in every case, whilst in contact with a glass cone the coagulation time is 12 minutes.

What is claimed is:

1. A polyurethane which can be used in particular for the production of articles intended to be in contact with blood, characterized in containing a macromolecular chain comprising nitrogen atoms in the form of quaternary ammonium groups, to which molecules of heparin are bonded, these nitrogen atoms originating from polymers consisting of $q$ recurring units of the formula:

$$-A-NH-CO-O-B-O-CO-NH- \quad (I)$$

and $t$ recurring units of the formula:

$$-A-NH-CO-Z-NH- \quad (II),$$

these units of the formula (I) and (II) being bonded to on another, and the various symbols of these units having the following meanings:

A is a divalent organic radical consisting of a straight-chain or branched-chain alkylene radical containing from 3 to 10 carbon atoms, or a cycloalkylene radical having 5 or 6 carbon atoms in the ring or a phenylene radical which is optionally substituted by 1, 2 or 3 lower alkyl radicals (with at most 4 carbon atoms), or two alkylene or phenylene radicals linked to one another by a divalent hydrocarbon radical containing from 1 to 4 carbon atoms or by a hetero-atom chosen from amongst oxygen, sulphur and nitrogen, B represents a divalent organic radical obtained by removing the terminal hydroxyl groups from a macrodiol of the formula:

$$HO+(B_1-O)_n-R-N-R-(O-B_1)_m-O\}_p B_1-OH \quad (III)$$
$$\phantom{HO+(B_1-O)_n-R-N}|$$
$$\phantom{HO+(B_1-O)_n-R-N}R_1$$

in which:

$B_1$ represents a linear or branched aliphatic radical having from 2 to 12 carbon atoms, R represents an alkylene radical of from 1 to 4 carbon atoms, $R_1$ represents an alkyl radical of from 1 to 20 carbon atoms which may contain functional groups, such as, for example, aldehyde, carboxylic acid or sulphonic acid groups, $n$, $m$ and $p$ are identical or different integers (or fractions in the case where (III) represents a mean formula) such that the molecular weight of B is between 300 and 10,000, and $q$ and $t$ are such that the polyurethane, before quaternization of the nitrogen atoms, has a specific viscosity, measured at 20° C on a solution of 2 g/l in dimethyl formamide, of greater than 0.05 and preferably between 0.1 and 0.9, ratio $q/t$ being between 0.5 and 10, Z is a single bond or a divalent radical chosen from amongst the radicals of the formulae: $-NH-NH-CO-$, $-NH-CH_2-CO-NH-NH-CO-$, $-NR_2-D-NR_3-CO-$, and $-O-M-O-CO-$, in which $R_2$ and $R_3$, which may be identical or different, are hydrogen atoms or lower alkyl radicals, D is a hydrocarbon chain containing from 2 to 12 carbon atoms, or a hydrocarbon ring with 5 or 6 carbon atoms or a nitrogen-containing heterocyclic ring with 5 or 6 chain members, containing 1 or 2 nitrogen atoms, all the hydrocarbon chains and rings being saturated or unsaturated, unsubstituted or substituted by one or two lower alkyl radicals or by a nitrogen-containing heterocyclic ring with 5 or 6 chain members, which is attached by a nitrogen atom, it being possible for two of the chains or rings to be linked to one another by an alkylimino group, and M is an aliphatic hydrocarbon radical containing from 2 to 12 carbon atoms, which is linear or branched, saturated or ethylenically unsaturated, unsubstituted or substituted by one or two lower alkyl radicals or by a dialkylamino radical, which is uninterrupted or interrupted by an alkylimino radical.

2. A polyurethane according to claim 1, characterized in that it comprises $t$ units of the formula (II) and $q$ units of the formula $$\begin{array}{c} R_4 X^\ominus \\ | \\ -A-NH-CO-O+(B_1-O)_n-R-\overset{\oplus}{N}- \\ | \\ R_1 \\ R-(O-B_1)_m-O\}_p B_1-O-CO-NH- \end{array} \quad (IV)$$

in which $R_4$ represents a monovalent or polyvalent organic radical and if R is monovalent, it may represent an alkyl, cycloalkyl or aralkyl radical which may possess functional groups and preferably containing fewer than 15 carbon atoms, these radicals being preferably the methyl, ethyl, propyl, cyclohexyl, benzyl and formylmethyl radicals, whilst if R is polyvalent it may represent an alkylene or alkenylene or cycloalkylene or aralkylene radical and then links different atoms of different macromolecular chains, and $X^-$ is an anion, which anion may be replaced by another anion in accordance with the usual ion exchange techniques and is preferably an anion such as a halide (chloride, bromide or iodide), nitrate, sulphate, sulphite, phosphate, sulphonate and hydroxyl.

3. A polymer according to claim 1, characterized in that Z is $$-NH-CH_2-CO-NH-NH-CO-.$$

4. A polymer according to claim 1, characterized in that it contains from 0.1 to 30 parts by weight of heparin per 100 parts of polymer.

5. A polymer according to claim 4, characterized in that it contains 16 to 30 parts by weight of heparin per 100 parts of polymer.

6. A process for the preparation of a polymer as defined in claim 1, which consists essentially of subjecting a polyurethane comprising units of the formula (I) and (II) to a quaternization treatment, and then keeping the polymer which has been treated in this way in contact with a heparin solution, preferably in the form of an alkali metal salt thereof.

7. A process for the preparation of a polymer as defined in claim 1, wherein the quaternization of the polyurethane is carried out with an alkyl halide.

8. A process for the preparation of a polymer as defined in claim 1, wherein the quaternization of the polyurethane is carried out in part with an alkyl halide and in part with a sultone.

9. A mixture of a polymer as defined in claim 1, with an anionic polyelectrolyte.

10. A mixture of a polymer as defined in claim 1, with a polyelectrolyte containing sulphonic acid groups.

11. A mixture of a polymer as defined in claim 1, with a sulphonated polysulphone.

12. A shaped article intended to be kept in contact with the blood, characterized in that it consists of a polymer as defined in claim 1.

13. A shaped article intended to be kept in contact with the blood, characterized in that it consists of a polymer as defined in claim 1 in admixture with an anionic polyelectrolyte.

14. A shaped article intended to be kept in contact with the blood, characterized in that it consists of a polymer as defined in claim 1 in admixture with a polyelectrolyte containing sulphonic acid groups.

15. A shaped article intended to be kept in contact with the blood, characterized in that it consists of a polymer as defined in claim 1 in admixture with a sulphonated polysulphone.

16. A process for the heparination of polymers carrying quaternary ammonium groups in solution in polar aprotic solvents, characterized in that the heparination is carried out in the presence of water and of a solvent chosen from the group consisting of dimethylsulphoxide (DMSO) and diethylene glycol (DEG).

17. A process according to claim 16, characterized in that the treated polymer is a polyurethane carrying quaternary ammonium groups.

18. A process according to claim 17, characterized in that in polyurethane treated is a polymer as defined in claim 1.

19. A process according to claim 16, characterized in that the heparin is in the form of Na salt.

20. A process according to claim 16, characterized in that the treated polymer is used in solution in a polar aprotic solvent.

21. A process according to claim 20, wherein the polar aprotic solvent is DMF or DMAc.

22. A process according to claim 16, characterized in that per 100 parts of heparin, 50 to 1,000 parts of water and 50 to 1,000 parts of dimethylsulphoxide (DMSO) or diethylene gylcol (DEG) are used.

23. A process according to claim 22, characterized in that per 100 parts of heparin, between 100 and 200 parts of water and between 300 and 1,000 parts of DMSO are used and in that the ratio of parts of water/parts of DMSO or DEG is less than 1.

* * * * *